United States Patent [19]

Rubino

[11] 4,025,615

[45] May 24, 1977

[54] ANTIPERSPIRANT COMPLEXES FORMED WITH ALKALI METAL AND AMMONIUM ZIRCONYL CARBONATES

[75] Inventor: Andrew M. Rubino, New Providence, N.J.

[73] Assignee: Armour Pharmaceutical Company, Phoenix, Ariz.

[22] Filed: Feb. 25, 1975

[21] Appl. No.: 552,823

[52] U.S. Cl. .............................. 424/46; 260/429.3; 424/47; 424/65; 424/66; 424/67; 424/68; 424/69
[51] Int. Cl.$^2$ .......................................... A61K 9/14
[58] Field of Search ................. 423/419, 420, 421; 424/66, 68

[56] References Cited

UNITED STATES PATENTS

| | | | |
|---|---|---|---|
| 2,316,141 | 4/1943 | Wainer | 423/419 |
| 2,507,128 | 5/1950 | Wainer | 423/419 |
| 2,508,787 | 5/1950 | Grote et al. | 424/68 |
| 2,571,030 | 10/1951 | Govett et al. | 424/68 X |
| 2,814,585 | 11/1957 | Daley | 424/66 |
| 2,854,382 | 9/1958 | Grad | 424/66 |
| 3,510,254 | 5/1970 | Bell | 423/419 |
| 3,551,095 | 12/1970 | Blumenthal | 423/419 |
| 3,553,316 | 1/1971 | Rubino | 424/66 |
| 3,555,146 | 1/1971 | Jones et al. | 424/66 |
| 3,557,025 | 1/1971 | Emerson et al | 423/419 |
| 3,903,258 | 9/1975 | Siegal | 424/66 |

FOREIGN PATENTS OR APPLICATIONS 780,283  3/1968  Canada .............................. 423/420

*Primary Examiner*—Dale H. Ore
*Attorney, Agent, or Firm*—Frank T. Barber; William W. Schwarze

[57] ABSTRACT

Alkali metal and ammonium zirconyl carbonates (AZC) may be used as active antiperspirant ingredients when converted to complexes with various acidic antiperspirant agents, including particularly the highly acidic zirconium compounds. The acidic antiperspirant agent activates the zirconium in the zirconyl carbonate to an acidic, active antiperspirant species. The zirconyl carbonate comprises about 2 to 35 weight percent of the complex, and the antiperspirant activating agent is present in such an amount that the pH of a 5 to 20 weight percent aqueous solution of the complex will be about 3 to 6. Potassium and ammonium zirconyl carbonates are preferred, but sodium may also be used if the complex is kept in solution. The acidic, antiperspirant activating agent is preferably a zirconium oxy salt or zirconium hydroxy salt, such as a zirconium hydroxy halide. However, other water soluble, polyvalent metal salts of strong acids may be used, particularly aluminum halides and basic aluminum compounds. In addition, the complex may include organic complexing agents such as urea, amino acids and hydroxy carboxylic acids. The complexes may be used in various conventional antiperspirant forms, including aqueous solutions, aerosol sprays, powder-in-oil aerosol sprays, creams, lotions, cream sticks, etc.

12 Claims, No Drawings

ANTIPERSPIRANT COMPLEXES FORMED WITH ALKALI METAL AND AMMONIUM ZIRCONYL CARBONATES

BACKGROUND OF THE INVENTION

The present invention relates to alkali metal and ammonium zirconyl carbonate (AZC) complexes useful as antiperspirants. More particularly, the invention is directed to zirconium antiperspirant systems in which alkali metal and ammonium zirconyl carbonates provide the primary or distinguishing source of active zirconium.

It has been known in the art for some time that zirconium salts provide exceptionally effective antiperspirant properties. Such zirconium compounds have included particularly the acidic zirconium salts, such as zirconium oxy chloride or zirconyl chloride, zirconium hydroxy chloride, and other halide and sulfate substitutes of the salts. However, the zirconium salts are extremely acidic and irritating to the skin. For example, a solution or zirconyl chloride which is effective as an antiperspirant has a pH of only about 0.8 and a solution of zirconyl hydroxy chloride which is effective as an antiperspirant has a pH of only about 1.2. As a result, it is necessary to buffer these solutions up to a pH which is suitable for application to the human skin, i.e., up to at least about 3 to 5.

In the buffering process, it is strongly believed that irreversible chemical reactions occur between the zirconium salts and the respective buffers, yielding new complexes. A number of prior attempts have been made in the art to buffer solutions of zirconium salts of to form zirconium complexes which take advantage of the effectiveness of zirconium compounds. One early attempt included the development of sodium zirconium lactate for use in cologne-stick type formulations. This lactate complex salt was sufficiently alkaline (pH 8.5), but was ineffective as an antiperspirant, and was repeatedly implicated in the generation of zirconium granulomas in some users.

Other attempts to make use of the acidic zirconium salts involved the buffering of solutions of these salts with urea (see U.S. Pat. No. 2,814,584 to Daley) or water soluble amino acids (see U.S. Pat. Nos. 2,814,585 to Daley and 2,854,382 to Grad) or aluminum hydroxy halides (see U.S. Pat. No. 2,906,668 to Beekman).

More recently, various derivatives have been formed incorporating zirconium compounds, including the amine-amide derivatives of U.S. Pat. No. 3,407,254 to Siegal et al., and the polyhydroxy derivatives of U.S. Pat. No. 3,405,153 to Jones and Rubino.

In addition, my copending application Ser. No. 418,712, filed Nov. 23, 1973, entitled "Aluminum-Zirconium Anti-Perspirant Systems With Salts Of Amino Acids", and other related copending applications describe other systems in which amino acids and other buffers have been incorporated in aluminum-zirconium complexes to offset the acidity of the zirconium and aluminum as well as provide other advantages to the antiperspirant. Nevertheless, still more efficient and advantageous methods are being sought to combat the acidity of aluminum and/or zirconium, while at the same time maintaining or improving antiperspirant efficacy.

BRIEF SUMMARY OF THE INVENTION

According to the present invention, alkali metal and/or ammonium zirconyl carbonates (hereinafter often referred to simply as AZC or sometimes referred to as alkaline zirconyl carbonates) may be used to form astringent compositions useful as antiperspirants. AZC is reacted with an acidic, antiperspirant activating agent to form a stable, water soluble complex in which the zirconium in the AZC is converted to an acidic, active antiperspirant species. The AZC is present in the complex in an amount of about 2 to 35 weight percent of the complex, and the acidic, antiperspirant activating agent is present in such an amount that a 5 to 20 weight percent (solids bases) aqueous solution of the complex will be about 3 to 6.

The preferred AZC compounds for use in the present invention are the ammonium zirconyl carbonates and potassium zirconyl carbonate. However, if kept in aqueous solution, effective complexes may also be formed with sodium zirconyl carbonate.

The acidic, antiperspirant activating agents include particularly the water soluble, polyvalent metal salts of strong acids, particularly strong mineral acids. Many such metal salts have been known in the art for their own antiperspirant activity. Particularly preferred are the zirconium compounds including zirconium oxy salts, zirconium hydroxy salts and basic zirconium-amino acid compounds. By using such zirconium compounds, complexes may be formed in which the sole active antiperspirant metal is zirconium, and the zirconium may comprise about 8 to 30 weight percent of the complex.

Other polyvalent metal salts which may be used as the acidic antiperspirant activating agent include aluminum compounds, such as aluminum chlorides and basic aluminum salts; alkaline earth metal salts, such as calcium and magnesium halides; and zinc compounds, such as zinc halides, sulfate, nitrate, etc.

In addition to the acidic antiperspirant activating agents, the complexes of the present invention may also include organic complexing agents for the purpose of buffering or otherwise modifying the complexes, such as to render them more stable. Suitable organic complexing agents for the AZC complexes may include urea, amino acids, alkaline and hydroxy salts of amino acids, hydroxy carboxylic acids, aluminum chelates of hydroxy carboxylic acids, and mixtures thereof.

The AZC complexes of the present invention will exhibit a pH of about 3 to 6 when dissolved in aqueous media to the extent of about 5 to 20 weight percent on a solids bases. The complexes may be used in a wide variety of conventional antiperspirant forms, including lotions, creams, roll-ons, aerosol sprays, and powder-in-oil aerosol sprays.

Except as otherwise indicated, as used herein, the term "suspension" (or suspending) will be broadly understood to include dispersions (or dispersing) and solutions (or dissolving), as well as suspensions themselves. Also, as used herein, the term "stably soluble" will be understood to means soluble in the given medium to the extent of at least about 10 percent by weight for indefinite periods of time without significant separation, settling or precipitation of the solute.

DETAILED DESCRIPTION OF PREFERRED EMBODIMENTS

The alkali metal and ammonium zirconyl carbonates (AZC) useful in preparing the complexes of the present invention include particularly potassium zirconyl carbonate, ammonium zirconyl carbonate and mixtures thereof. Particularly preferred is ammonium zirconyl carbonate, which may also be referred to as ammonium zirconium carbonate or ammonium carbonate-zirconate. For ease of reference in the remainder of this specification, the zirconyl carbonates will be referred to as AZC, or ammonium zirconyl carbonate will be specifically referred to, but it will be understood that in most cases the other zirconyl carbonates or mixtures could be substituted.

It should be noted that ammonium zirconium carbonate exists in solution form only, and cannot be reconstituted to a stable solution after drying to a powder. Potassium zirconyl carbonate can be reconstituted to a stable solution if it is carefully dried. Moreover, complexes of the present inventionn formed with sodium zirconyl carbonate cannot be reconstituted to a stable solution if the complex is dried to a powder form. However, upon formation in aqueous solution, the complexes of the present invention are stably soluble in aqueous media.

AZC may be prepared by several known methods. The preferred method, which was used in preparing the various forms of AZC used in the specific examples set forth below, is described in German Pat. No. 2,251,434, issued May 3, 1973 to Magnesium Elektron Ltd., entitled "Aqueous Solution Of Potassium Zirconium Carbonate And Ammonium Zirconium Carbonate, Preparation Process And Application". An alternate method of preparation for ammonium zirconyl carbonate is described in U.S. Pat. No. 3,418,073 to Blumenthal.

Also, according to W. B. Blumenthal, *The Chemical Behavior Of Zirconium*, D. Van Nostrand Company, Inc. (1958) at page 195, ammonium zirconyl carbonate may be prepared by the reaction of ammonium carbonate with carbonated trioxidizirconium hydroxide heptahydrate ($Zr_2O_3(OH)_2.CO_2.7H_2O$), known commercially as carbonated hydrous zirconia. Carbonated hydrous zirconia is commercially available or may be formed by precipitation from reacting zirconyl chloride with sodium or calcium carbonate or by other methods. Potassium zirconyl carbonate may be used by analogous preparations. In any event, the AZC compounds are commercially available.

Ammonium zirconyl carbonate is a water soluble complex of zirconium which may appear in several different forms. Two of the better known forms may be represented by the following formulas:

(1) 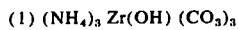 $(NH_4)_3 Zr(OH) (CO_3)_3$ (2) 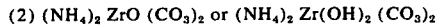 $(NH_4)_2 ZrO (CO_3)_2$ or $(NH_4)_2 Zr(OH)_2 (CO_3)_2$ The first of the above variations is referred to as the tri-ammonium tri-carbonato version, and the latter may be referred to as the di-ammonium di-carbonato form. Of course, it will be understood that the above formulas are greatly simplified and do not show features such as water of hydration, polymer or complex forms, structural variations, etc. However, all forms and variations of AZC are contemplated within the scope of the present invention, including substitutions, such as shown in formula (2) above, where two hydroxyl groups replace and oxo group linked to zirconium.

AZC by itself does not have significant antiperspirant activity for general antiperspirant use. Thus, AZC is anionic in nature and aqueous solutions of AZC alone have an alkaline pH, whereas ingredients generally recognized to be effective antiperspirants are cationic in nature and yield solutions having an acidic pH of about 3 to 6, and preferably about 3 to 5.

However, according to the present invention, it has been found that the zirconium in AZC may be converted to an acidic active antiperspirant species with various compounds, which for ease of reference are herein referred to as antiperspirant activating agents or acidic, antiperspirant activating agents. These agents render the AZC stably soluble in water by forming complexes with AZC. At the same time, the activating agents decrease the pH of an AZC solution to the range of about 3 to 6, and preferably about 3 to 5. This acid pH ensures that the zirconium and any other antiperspirant metals which may be employed, will be in an active antiperspirant state.

A number of antiperspirant activating agents which meet the above criteria are readily available and known from the prior antiperspirant art. Other more recently developed and unkonwn antiperspirant ingredients may also be used.

the activating agent may have various degrees of antiperspirant efficacy in intslf and therefore be used to complement the antiperspirant efficacy of the zirconium in the AZC. In fact, such active antiperspirant ingredients may, if desired, be used as the major antiperspirant ingredient in the complexes of the present invention, in which case the alkaline zirconyl carbonates would fulfill a novel supplementary and buffering roll in the complexes. Such activating agents would include any of a number of compounds and complexes containing aluminum, zirconium and/or zinc, which are all known and conventionally used inthe antiperspirant art for their antiperspirant efficacy. These compounds may be generally classified as water soluble, polyvalent metal salts of mineral acids, particularly strong mineral acids, such as the zirconium, aluminum and zinc salts of hydrochloric, sulfuric and nitric acids.

In addition, certain magnesium and calcium compounds, which primarily function as buffers may also contribute to the antiperspirant efficacy when used as complexing agents in the present invention, as indicated for example in my copending applications Ser. No. 411,995, filed Nov. 1, 1973, entitled "Basic Magnesium-Aluminum Compositions Useful As Antiperspirants" and Ser. No. 489,320, filed July 17, 1974, entitled "Aluminium-Zirconium Antiperspirant Systems With Trace Amounts Of Alkaline Earth Metals", new U.S. Pat. No. 3,998,788.

In addition to the antiperspirant activating agents, complexing agents may be used which have no appreciable antiperspirant efficacy in themselves, but which are known or have been recently developed for use as buffers in various antiperspirant systems. Complexing agents of this type include certain organic acids, salts of organic acids and other organic compounds such as urea. Of course, complexing agents which are a combination of active antiperspirant metal and organic acid buffer, such as the aluminum chelates of hydroxy carboxylic acids, may also be used. More specific examples of complexing agents useful in the present invention are discussed below, although the following list is not intended to be exhaustive or exclusive.

The aluminum compounds useful as activating agents in forming the antiperspirant comlexes of the present invention including aluminum halides, such as aluminum chloride ($AlCl_3$), and basic aluminum compounds and complexes which are known in the antiperspirant art for their antiperspirant effectiveness and other properties. Aluminum chloride has been known for many years as one of the most effective antiperspirant compositions available. However, the use of aluminum chloride alone has been necessarily limited, due to the extreme acidity of even weak aluminum chloride solutions.

However, when complexed with AZC according to the present invention, aluminum chloride is buffered to yield effective antiperspirant solutions having an acceptable pH of at least about 3. For example, when aluminum chloride is reacted with ammonium zirconyl carbonate, and optionally an organic buffer, complexes are formed which have a suitable buffered acidity as well as containing both aluminum and zirconium as antiperspirant ingredients.

The basic aluminum compounds which may be used in forming the complexes of the present invention includes the conventional basic aluminum salts which have been known to the antiperspirant art for some time, and which have a degree of antiperspirant efficacy in their own right, as a result of the presence of the active aluminum ion. These basic aluminum salts may be represented by the following general empirical formula:

$$Al_2(OH)_{6-nx} A_x$$

wherein $x$ may vary from greater than 0 to less than 6, $6-nx$ is greater than or equal to 0, $n$ is the valence of A, and A is selected from the group consisting of halides, nitrate, sulfamate, sulfate and mixtures thereof.

It will of course be understood that the above formula is greatly simplified and is intended to represent and include basic aluminum compounds containing coordinated and/or bound molecules of water as well as polymers, complexes and mixtures of the above basic formula.

Particularly preferred basic aluminum compounds of the above formula are the 2/3 and 5/6 basic aluminum chlorides, in which A is chloride and $x$ is between about 1 and 2 and need not be an integer. Thus, such basic aluminum chlorides may be represented by the formulas $$Al_2(OH)_5CL \text{ and } Al_2(OH)_4Cl_2.$$

The basic aluminum chlorides are also referred to as aluminum chlorhydroxide or aluminum chlorhydrate or aluminum hydroxy chloride, and are commercially available from Reheis Chemical Company, Division of Armour Pharmaceutical Company under the trademark "Chlorhydrol".

In addition to the simple basic aluminum salts indicated above, complexes or derivatives of the basic aluminum salts may also be used advantageously in the complexes of the present invention. Examples of such derivatives or complexes include the phenolsulfonate derivatives described in U.S. Pat. No. 3,634,480 to Sheffield. Such complexes are formed by reacting 5/6 basic aluminum chloride with phenolsulfonic acid, zinc phenolsulfonate or aluminum phenolsulfonate. Other suitable derivatives and complexes of basic aluminum salts which may be used in the complexes of the present invention will be readily apparent to those of ordinary skill in the art in view of the present specification.

The zirconium compounds which are useful as activating agents in forming the complexes of the present invention include both the zirconium oxy salts and zirconium hydroxy salts, also referred to as the zirconium salts and zirconyl hydroxy salts. These compounds may be represented by the following general empirical formula:

$$ZrO(OH)_{2-nz} B_z$$

wherein $z$ may vary from about 0.9 to 2 and need not be an integer, $n$ is the valence of B, $2-nz$ is greater than or equal to 0, and B may be the same as A in the previous formula, that is B may be selected from the group consisting of halides, nitrate, sulfamate, sulfate and mixtures thereof. Although only zirconium compounds are examplified in this specification, it will be understood that other Groups IV B metals, including hafnium could be used to form the complexes of the present invention.

As with the basic aluminum compounds, it will be understood that the above formula is greatly simplified and is intended to represent and include compounds having coordinated and/or bound water in various quantities, as well as polymer, mixtures and complexes of the above. As will be seen from the above formula, the zirconium hydroxy salts actually represent a range of compounds having various amounts of the hydroxyl group, varying from about 1.1 to only slightly greater than 0 groups per zirconium atom.

Particularly preferred zirconium compounds for use in the present invention include zirconyl chloride (also referred to as basic zirconium chloride or zirconium oxy chloride) and zirconyl hydroxy chloride, which may be represented by the simple formulas $ZrO Cl_2$ and $ZrO(OH)Cl$, respectively. These compounds are commercially available in solution form. In the alternative, the zirconium compounds can be made by dissolution of commercially available zirconium carbonate paste (carbonated hydrous zirconia) in the appropriate amount of the acid of the anion to be used, e.g., hydrochloric acid. Other useful zirconium salts will be apparent to those of ordinary skill in the art, such as trioxodizirconium hydroxy halides and similar salts described, for example, in U.S. Pat. No. 2,837,400 to Blumenthal, and the basic zirconium glycinates and similar basic zirconium-amino acid complexes described in the copending application Ser. No. 562,300 of Rubino, Jones and Brethschneider, filed Mar. 26, 1975, entitled "Basic Zirconium Complexes And Methods Of Making And Using In Antiperspirants".

Suitable magnesium compounds for incorporation into the complexes of the present invention include magnesium halides, complexes sulfate, and magnesium-amino acid salts (such as magnesium glycinate), and mixtures thereof. Suitable zinc compounds for incorporation into the complexex of the present invention include zinc halides, zinc sulfate, zinc nitrate, zinc sulfamate, zinc phenolsulfonate and mixtures thereof. Other magnesium and zinc compounds having known antiperspirant advantages will be evident to those of ordinary skill in the art.

The organic compounds which are useful as complexing agents informing the complexes of the present invention include urea and the so-called neutral amino acids, i.e., amino acids in which the number of amino groups is equal to the number of carboxyl groups in the molecule. Urea has been previously disclosed as a buffer in aqueous zirconium containing antiperspirant systems in U.S. Pat. No. 2,814,584 to Daley, and neutral amino acids have previously been disclosed as buffers in aqueous zirconium containing antiperspirant systems in U.S. Pat. Nos. 2,814,585 to Daley and 2,854,382 to Grad, all of these patents being assigned to The Proctor & Gamble Company. The disclosures of each of these patents and incorporated herein by reference.

Also suitable as complexing agents in the present invention are the salts of the above amino acids. Such salts are described as buffers in my copending applications Ser. No. 431,639, filed Jan. 8, 1974, entitled "Zirconium-Aluminum-Polyol Buffered Antiperspirant Complexes", now U.S. Pat. No. 3,981,986, and Ser. No. 418,712, filed Nov. 23, 1973, entitled "Aluminum-Zirconium Antiperspirant Systems With Salts Of Amino Acids", the disclosures of which are incorporated herein by reference.

Among the salts of amino acids which may be used in the present invention are those derived from the so-called natural amino acids, i.e., amino acids in which the number of amino groups is equal to the number of carboxyl groups in the molecule. Examples of such amino acids include glycine, DL-valine, β-alanine, arginine and L-(=)-proline and mixtures thereof. The corresponding salts are the glycinates, DL-valinates, β-alaninates, argininates and L-(−)-prolinates suitable salts of other amino acids useful in the present invention will be evident to those of ordinary skill in the art in view of this specification.

The particular salts of amino acids which may be used include both alkaline and hydroxy salts. As used herein, the term "alkaline" as applied to salts of amino acids is not intended to be limited to those having a pH of greater than 7.0, since some complex or not perfectly neutralized salts may have pH's less than 7.0 (e.g., 6.0 or 6.5) and still be useful in this invention. Instead, alkaline is merely meant to refer to the usual alkali and alkaline earth cations, including ammonium. For example, suitable alkaline salts include sodium, potassium, ammonium, magnesium and calcium salts of the above-mentioned amino acids. These salts may be obtained commercially or prepared by reacting the particular amino acid in aqueous solution with the carbonate or hydroxide of the particular alkali or alkaline earth metal.

Suitable hydroxy salts of amino acids which may be used in the present invention include the dihydroxy and monohydroxy aluminum salts of amino acids and the so-called aluminum-magnesium-hydroxy-glycine compounds. Essentially, these hydroxy salts are the reaction products of aluminum hydroxy antacids with the appropriate amino salt. For example, the dihydroxy and monohydroxy aluminum salts may be obtained commercially or prepared by reacting the amino acid with aluminum hydroxide ($Al(OH)_3$) gels in aqueous solution with agitation and heat. See for example u.s. Pats. No. 2,588,090 to Delmar and No. 2,480,743 to Krantz et al.

Other organic compounds useful as complexing agents in forming the complexes of the present invention include the hydroxy carboxylic acids. Suitable hydroxy carboxylic acids (also referred to as hydroxy acids) include the organic acids having a hydroxyl group alpha and/or beta to the carboxylic acid radical. Examples of such acids include lactic, citric, tartaric, glycolic, gluconic, trihydroxy glutaric, citryl trigluconic, citryl monogluconic, citryl digluconic, malic, tetrahydroxy adipic, and citramalic acids, and mixtures thereof. In general, the suitable hydroxy carboxylic acids are at least bidentate, and have a valence of from −1 to −4.

In addition, hydroxy carboxylic compounds described as buffers in my copending application Ser. No. 433,931, filed Jan. 16, 1974, entitled "Aluminum-Zirconium Antiperspirant Systems With Hydroxy Carboxylic Compounds", new U.S. Pat. No. 3,991,176, may also be used as complexing agents in the present invention. The disclosure of that application is incorporated herein by reference.

Particular hydroxy carboxylic compounds therein described and useful in the present invention include non-toxic salts of hydroxy carboxylic acids, non-toxic salts of aluminum chelates of hydroxy carboxylic acids, codried mixtures of aluminum hydroxide with non-toxic salts of aluminum chelates of hydroxy carboxylic acids, and mixtures thereof. It is believed that the salts of hydroxy carboxylic acids, even if insoluble in water, form complexes with zirconium compounds and basic aluminum compounds, which complexes are soluble in water. Moreover, since the complexes of the present invention may be dried to a solid powder form, it is not necessary that the complexes be stable in aqueous solution for any great length of time, except when it is desired to redissolve the powder for use in solution form. However, redissolution is highly desirable, since failure to redissolve may indicate degradation of the complex and loss of antiperspirant activity.

As used herein, the term "non-toxic salts" is intended to include those salts or compounds in which one or more non-toxic cations are reacted with hydroxy carboxylic acids and/or aluminum chelates of hydroxy carboxylic acids. The non-toxic cation may include the alkali metals, such as sodium and potassium, the alkaline-earth metals, such as magnesium and calcium, as well as zinc, zirconium, aluminum and ammonium.

Among the non-toxic salts which may be used to form the complexes of the present invention are those derived directly from the above-mentioned hydroxy carboxylic acids. It will be understood that the hydroxy carboxylic salts may contain either or both forms of the same ligand derived from the hydroxy carboxylic acid, one form corresponding to the form of the acid in which both the carboxyl and hydroxyl groups have been neutralized, and the other form corresponding to that form of the acid in which only the carboxyl groups have been neutralized, and whose hydroxyl group may be coordinated to a cation.

The non-toxic salts of hydroxy carboxylic acids may be obtained commercially or prepared by reacting the desired hydroxy carboxylic acid with the hydroxide, oxide, carbonate, or bi-carbonate of the desired non-toxic cation. Such reaction may be carried out simply in aqueous solution a the appropriate heat and stoichiometric amounts. Examples of suitable non-toxic salts of hydroxy carboxylic acids which may be used in forming the complexes of the present invention, and which are illustrated in the specific examples below, include sodium lactate, magnesium glycolate, potassium tartrate and calcium gluconate. Other suitable non-toxic salts of hydroxy carboxylic acids useful in the present invention will be evident to those of ordinary skill in the art in view of this specification.

In addition to the non-toxic salts derived directly from hydroxy carboxylic acids, the complexes of the present invention may also contain non-toxic salts derived from aluminum chelates of hydroxy carboxylic acids. These salts or compounds are described in detail in U.S. Pat. No. 3,553,316, issued Jan. 5, 1971 to Rubino for "Anti-perspirant Compositions Containing Aluminum Chelates of Hydroxy Carboxylic Acids." the disclosure of U.S. Pat. No. 3,553,316 is incorporated herein by reference.

Particularly preferred salts of aluminum chelates of hydroxy carboxylic acids useful in forming the complexes of the present invention include sodium aluminum hydroxy lactate, available from Reheis Chemical Company division of Armour Pharmaceutical Company under the name of "Nalac", and sodium aluminum chlorhydroxy lactate, available from Reheis under the trademark "Chloracel".

In all of the above complexes, the alkaline zirconyl carbonates have the advantages of serving a dual function. First of all, they serve as a source of zirconium, which is a known active antiperspirant ingredient. Secondly, they serve as a buffer to raise the pH of the normally highly acidic zirconium systems. Similarly, the more acidic lower basic aluminum chloride systems can be buffered to more equable levels (i.e., a pH of at least about 3) with the alkaline zirconyl carbonates to yield combination aluminum-zirconium complex systems.

In addition, since the alkaline zirconyl carbonates may be complexed with various zirconium compounds, as indicated above, it is now possible to form antiperspirant systems including only zirconium as the active antiperspirant ion. Although zirconium is the most effective antiperspirant metal known today, it is extremely acidic, therefore requiring heavy buffering. In the past, it has been necessary to use various basic aluminum compounds to accomplish part of this buffering, with the remainder of the buffering being accomplished by various organic compounds such as urea and amino acids. Thus, the use of an organic buffer alone, without aluminum, would require much too great an amount of the organic buffer.

The organic buffers used as complexing agents in the present invention, although they may not possess any independent antiperspirant effect, are useful and sometimes necessary to achieve proper reaction or solubility between the AZC and certain aluminum and zirconium activating agents. For example, the AZC cannot be directly reacted with 5/6 basic aluminum chloride to form soluble species. Accordingly, a hydroxy carboxylic acid or other complexing agent must also be used to assist in the formation of a soluble complex. Similarly, the reaction of solubility with ammonium zirconyl carbonate and zirconyl hydroxy chloride (ZrO (OH) Cl) is limited by the pH of the reaction mixture, and this may be assisted, for example, by the addition of a hydroxy carboxylic acid or similar complexing agent. Other advantages or situations requiring the use of an organic complexing agent or buffer will become evident to one of ordinary skill in the art upon routine experimentation with the systems of the present invention.

Generally, the AZC should be present in the complexes of the present invention in an amount of about 2 to 35 weight percent of the complex. The total amount of zirconium in the complex, whether from the AZC or zirconium complexing agents, should comprise about 2 to 40 weight percent of the complex, and preferably about 8 to 30 weight percent of the complex. When dissolved in water or other aqueous media to the extent of about 5 to 20 weight percent, the complexes of the present invention yield a solution pH in the range from about 3 to 6.

As indicated previously it is possible with the complexes of the present invention to form antiperspirant systems in which zirconium is the only active antiperspirant metal, i.e., no aluminum or zinc or similar metals are present. However, where it is desired to use an aluminum compound as the complexing agent to form aluminum-zirconium antiperspirant systems, a wide range of Al/Zr mol ratios may be achieved. Preferred Al/Zr mol ratios lie in the range of about 1:10 to 10:1. Where high ratios of zirconium or even total zirconium systems are used, it is of course necessary to use larger amounts of either the alkaline zirconium carbonate or an organic buffer or a combination of both. However, the use of alkaline zirconium carbonates according to the present invention has the advantage that far less organic buffer is necessary than in previous zirconium antiperspirant systems. This is most important since the buffer is generally non-reactive, that is, it has no appreciable antiperspirant activity and to my knowledge does not enhance antiperspirant efficacy other than to provide a more suitable pH level. It is generally accepted that antiperspirant compositions must have a pH of at least about 3 and preferably about 3 to 5 in order to be satisfactory for application to the human skin.

The method of forming the complexes of the present invention is not particularly critical. In general, the complexes may be formed simply by adding the various components together in an aqueous solution and then, if desired, drying the solution to a dry powder. The various components are preferably added one at a time with stirring or agitation. Moderate heating, such as to a maximum of about 75° or 85° C. for several hours may be necessary or advantageous during or after the addition of certain ingredients, particularly when an insoluble compound is added or when a precipitate is formed after the addition of an ingredient. In addition, as previously indicated, it is sometimes necessary to first complex one of the metal compounds with an organic buffer before reacting with another metal compound, such as in the case where ammonium zirconyl carbonate is added to zirconyl hydroxy chloride. Thus, adjustment of pH is sometimes important to achieve proper solubility or reaction.

The drying step is also not particularly critical and may be carried out in a number of ways, including vacuum drying, oven drying, spray drying or freeze drying. It will be understood that drying does not mean that all of the water is removed, since a certain amount of water should remain in the complex as coordinated and/or bound water. Thus, drying to just past the point where the solution becomes a friable solid should be sufficient. If the complex is over dried, so that some of the coordinated and/or bound water is removed, the stability and/or activity of the complex may be interfered with, and the complex may not be readily redissolvable in solvents, particularly hydroalcoholic solvents.

While it has been indicated that the reaction process is not considered particularly critical, it will be understood that sufficient time, heat and agitation are needed to allow reaction of the alkaline zirconyl carbonates with the various complexing and activating agents to form the new complexes of the present invention. Also, it will be understood that not all complexing and activating agents in the classes listed above are suitable for reaction with all types of AZC. For example, other types of AZC besides potassium and ammonium appear to form complexes with many activating and complexing agents, but after drying the complexes cannot be constituted in water. Examples of other systems which have been tried but could not be reconstituted in water after drying include glycine with ammonium zirconyl carbonate or potassium zirconyl carbonate; potassium zirconyl carbonate with zinc chloride; sodium zirconyl carbonate with trioxodizirconyl hydroxy chloride; etc.

The complexes of the present invention will now be illustrated in more detail with reference to the following specific, non-limiting examples. Except where otherwise indicated, all of the following examples were performed in aqueous media, and all percents are on a weight basis. The Al/Zr ratio is on a mol basis.

In the examples, three different forms of ammonium zirconyl carbonate were used. In the examples, the particular form used is indicated by the percentages of ammonium, carbonate and zirconium in the starting material, and these may be represented by the following empirical formulas and corresponding analyses:

| (a) | $(NH_4)_2ZrO(CO_3)_2$ or $(NH_4)_2Zr(OH)_2(CO_3)_2$ | |
|---|---|---|
| | Analysis: $NH_4^+$ - | 6.2% |
| | Zr - | 16.4% |
| | $CO_3^-$ - | 19.8% |
| (b) | $(NH_4)_5Zr(OH)(CO_3)_4$ | |
| | Analysis: $NH_4^+$ - | 6.3% |
| | Zr - | 6.8% |
| | $CO_3^+$ - | 15.0% |
| (c) | $(NH_4)_4ZrO(CO_3)_3$ or $(NH_4)_4Zr(OH)_2(CO_3)_3$ | |
| | Analysis: | |
| | $NH_4^+$ - | 4.4% |
| | Zr - | 5.8% |
| | $CO_3^-$ - | 9.3% |

Only one form of potassium zirconyl carbonate was used in the examples, and this may be represented by the following empirical formula and corresponding analysis:

| | $K_3Zr(OH)(CO_3)_3$ | |
|---|---|---|
| Analysis: | $K^+$ - | 10.6% |
| | Zr - | 7.4% |
| | $CO_3^-$ - | 13.2% |

Note that in the above formulas, the carbonate content is not equivalent to the alkali metal or ammonium content because some carbonate is present in the basic zirconyl carbonate which is reacted with the simple carbonate salts (e.g. $K^+$, $NH_4^+$, etc.) to form the soluble AZC compounds.

EXAMPLE I

Thirty grams of glucono-delta-lactone was reacted with 60 g. of an aqueous solution of 25% aluminum chlorhydroxide [$Al_2(OH)_5Cl$, 6.25% Al] by heating at 80° C. for 4 hours. After the above solution cooled, 30 g. of ammonium zirconium carbonate (6.2% $NH_4^+$, 16.4% Zr, 19.8% $CO_3^-$) was added. The solution was evaporated in an oven at 50° C. under a vacuum of 46 cm. of Hg. The product analyzed: 6.94% Al and 8.55% Zr (Al/Zr ratio = 2.7:1).

EXAMPLE II

Ten grams of ammonium zirconium carbonate (6.2% $NH_4^{++}$, 16.4% Zr, 19.8% $CO_3^-$) was dissolved in 28 g. of zirconyl chloride solution ($ZrOCl_2$, 14.1% Zr). The solution was then diluted with 200 g. of water prior to the addition of 12.5 g. of 50% aluminum chlorhydroxide solution (12.5% Al). The product was oven-dried at 45° C. under a vacuum of 45 cm. of Hg and found to contain 9.16% Al and 26.6% Zr (Al/Zr ratio = 1.0:1 ).

EXAMPLE III

Fifteen grams of 88% lactic acid was reacted with 30 g. of ammonium zirconium carbonate (6.3% $NH_4^+$, 6.8% Zr, 15.0% $CO_{31}^=$). The pH of this solution was 6.4, after one hour of agitation. The pH was lowered to 6.2 on the addition of 4 g. of $MgCl_2.6H_2O$. The product was oven-dried at 50° C. under a vacuum of 35 cm. of Hg and found to contain 8.88% Zr, 3.59% Mg and 66.1% lactic acid. A reconstituted 20 weight percent solution of the product in water had a pH of 6.2.

EXAMPLE IV

Five grams of ammonium zirconium carbonate (4.4% $NH_4^+$, 5.8% Zr, and 9.3% $CO_3^=$) was dissolved in 50 g. of 33⅓% zirconyl hydroxychloride solution (14.2% Zr), raising the pH of the solution to 1.5. The above solution was added to 60 g. of 50% basic aluminum bromide solution [$Al_2(OH)_5Br$, 10.2% Al]. The resulting clear solution was then diluted with 200 g. of water prior to the addition of 5 g. of zinc chloride, raising the pH to 3.6. The product was evaporated in an oven at 50° C. under a vacuum of 45 cm. of Hg. The product analyzed: 14.6% Al, 13.1% Zr and 4.9% Zr (Al/Zr ratio = 3.7:1).

EXAMPLE V

Five grams of ammonium zirconium carbonate solution (6.3% $NH_4^+$, 6.8% Zr, and 15.0% $CO_3^=$) was dissolved in 50 g. of zirconyl hydroxy bromide solution (14.1% Zr) with agitation. The solution was diluted with 100 g. of water prior to the addition of 10 g. of glycine. The pH of the resultant solution was 4.0. The product was oven-dried at 50° C. under a vacuum of 40 cm. of Hg and found to contain 28.7% Zr and 35.5% glycine.

EXAMPLE VI

Seven grams of ammonium zirconium carbonate (6.3% $NH_4^+$, 6.8% Zr, and 15.0% $CO_3^=$) was dissolved in 100 g. of zirconyl hydroxychloride solution (14.2% Zr) with agitation. The solution was diluted with 50 g. of water prior to the addition of 10 g. of glycine. The pH of the resultant solution was 3.2. The product was oven-dried at 50° C. under a vacuum of 40 cm. of Hg and found to contain 31.1% Zr and 25.9% glycine.

EXAMPLE VII

Forty grams of 44% lactic acid was added slowly with agitation to a solution of ammonium zirconium carbonate (3.2% $NH_4^+$, 3.4% Zr and 7.5% $CO_3^=$). The solution was reacted for 2 hours at room temperature to form a Zr-lactate complex.

Thirty grams of a basic zirconium glycinate gel (4.4% Zr. and 1.4% glycine) was dissolved in 100 g. of a zirconyl chloride solution (7.2% Zr) while heating at 80° C. The solution was cooled to room temperature and added to the Zr-lactate complex. The product was oven-dried at 45° C. under a vacuum of 35 cm. of Hg and found to contain 25.8% Zr, 35.8% glycine, 38.1% lactic acid.

EXAMPLE VIII

Five grams of potassium zirconium carbonate (10.6% K, 7.4% Zr and 13.2% $CO_3^=$) was dissolved in 60 g. of a zirconyl chloride solution (7.2% Zr). The solution was buffered with 10 g. of urea and then oven-dried at 52° C. under a vacuum of 43 cm. of Hg. The product analyzed: 23.7% Zr and 47.3% urea.

EXAMPLE IX

Thirty grams of potassium zirconium carbonate (10.6% K, 7.4% Zr and 13.2% $CO_3^=$) was reacted with 840 g. of trioxodizirconyl hydroxychloride solution (5.2% Zr). The solution was filtered to remove insoluble.

Two hundred forty grams of a 25% basic aluminum iodide solution [$Al_2(OH)_5I$, 4.15% Al] was buffered with 60 g. of β-alanine. The zirconium material described above was then added to this solution with agitation. The product was oven-dried at 53° C. under a vacuum of 50.5 cm. of Hg, and found to contain 1.05% Al, 29.2% Zr, and 38.1% β-alanine (Al/Zr ratio = 0.12:1). On reconstitution to 20% w/w, the pH of the solution was 5.3.

EXAMPLE X

Seven grams of ammonium zirconium carbonate (4.4% $NH_4^+$, 5.8% Zr, and 9.3% $CO_3^=$) was dissolved in 100 g. of 33⅓% zirconyl hydroxychloride solution (14.4% Zr).

Four hundred grams of 25% 5/6 basic aluminum phenolsulfonate solution (4.15% Al) was heated to 85° C. Five grams of $MgCl_2.6H_2O$ was dissolved in this hot solution prior to the slow addition of the zirconium solution described above. The product was oven-dried at 50° C. under a vacuum of 35 cm. of Hg and found to contain 10.6% Zr, 12.3% Al and 0.4% Mg (Al/Zr ratio = 2.8:1).

EXAMPLE XI

Twenty-five grams potassium zirconium carbonate (10.6% K, 7.4% Zr, and 13.2% $CO_3^=$) was dissolved in 250 g. of zirconyl iodide solution (4.83% Zr). The solution was diluted with 100 g. of water prior to the addition of 25 g. of glycine. This solution was then added to 40 g. of a 25% solution of 5/6 basic aluminum nitrate [$Al_2(OH)_5NO_3$, 5.7% Al]. The resultant solution's pH was 3.2. The product was oven-dried at 50° C. under a vacuum of 35 cm. of Hg and found to contain 11.8% Zr, 2.06% Al and 22.6% glycine (Al/Zr ratio = 0.5:1).

EXAMPLE XII

Twenty grams of ammonium zirconium carbonate (6.3% $NH_4^+$, 6.8% Zr and 15.0% $CO_3^=$) was dissolved in 400 g. of 33-⅓% zirconyl hydroxychloride solution (14.4% Zr).

Twenty grams of β-analine was dissolved in 103 g. of 2/3 basic aluminum sulfamate solution (4.8% Al) prior to the addition of the zirconium solution described above. The product was oven-dried at 45° C. under a vacuum of 41 cm. of Hg and found to contain 3.26% Al, 38.6% Zr and 13.1% β-alanine (Al/Zr ratio = 0.25:1).

EXAMPLE XIII

Five grams of potassium zirconium carbonate was dissolved (10.6% K, 7.4% Zr and 13.2% $CO_3^=$) in 200 g. of zirconyl hydroxychloride solution (7.2% Zr). This solution was then added slowly to 600 g. of ⅓ basic aluminum sulfate solution (3.1% Al) which was being heated at a constant 75° C. The solution was oven-dried at 50° C. under a vacuum of 35 cm. of Hg. The product analyzed: 15.3% Zr and 19.7% Al(Al/Zr ratio = 4.3:1).

EXAMPLE XIV

Six grams of ammonium zirconium carbonate (6.2% $NH_4^+$, 16.4% Zr, 19.8% $CO_3^=$) was dissolved in 50 g. of 24° Baume $AlCl_3$ (4.2% Al) prior to the addition of 5 g. of glycine. The material was oven-dried under a vacuum of 46.5 cm. of Hg at 58° C. The product analyzed as follows: 7.94% Al, 4.53% Zr, and 20.9% glycine (Al/Zr ratio = 6.0:1).

EXAMPLE XV

Twenty-five grams of ammonium zirconium carbonate (6.3% $NH_4^+$, 6.8% Zr, 15.0% $CO_3^=$) was reacted with 56 g. of 88% lactic acid. After thirty minutes of agitation, this solution was added to 16.1 g of 50% aluminum chlorhydroxide solution [$Al_2(OH)_5Cl$, 12.5% Al]. The solution was dried in an oven at 55° C. under a vacuum of 40 cm. of Hg. The product analyzed as follows: 2.8% Zr, 3.2% Al and 82.1% lactic acid (Al/Zr ratio = 4.0:1).

EXAMPLE XVI

Fifty grams of a Chloracel solution (sodium aluminum chlorhydroxy lactate complex; 3.95% Al and 10.5% lactic acid) was reacted with 10 g. of ammonium zirconium carbonate (6.3% $NH_4^+$, 6.8% Zr, and 15.0% $CO_3^=$). The pH of the resultant solution was 8.9. The solution was then divided into two parts and converted to the following antiperspirant systems:

a. To 30 grams of the solution was added 5 grams of 24° Baume aluminum chloride (4.2% Al), in order to reduce the pH of the solution to below 6.0 while at the same time incorporating active aluminum antiperspirant species. The product was dried in an oven at 60° C. under a vacuum of 45 cm. of Hg and analyzed: 10.3% Al, 3.30% Zr; 21.6% lactic acid (Al/Zr ratio = 10:1).

b. To the remaining 30 grams of the solution was added 5 grams of 33% zirconyl hydroxy chloride solution (14.1% Zr), in order to reduce the pH of the solution to below 6.0 while at the same time incorporating active zirconium species into the system. The product was dried in an oven at 60° C. under a vacuum of 45 cm. of Hg and analyzed: 8.3% Al; 10.2% Zr; 21.8% lactic acid (Al/Zr ratio = 2.8:1).

Among the advantages of the complexes of the present invention is that highly acidic aluminum, zirconium or aluminumzirconium antiperspirant systems may be effectively buffered with a complex which also provides an additional source of zirconium, a metal which is known for its antiperspirant efficacy. Moreover, due to the initially high pH of the alkaline zirconyl carbonates, much smaller amounts of amino acid or other organic buffer are required in the final complex than have been required in many prior art antiperspirant systems using aminio acids as buffers.

As indicated previously, the complexes of the present invention may be used in a variety of conventional antiperspirant forms which are applied to the human axilla for effective perspiration inhibition. In such formulations, the complex should be present in such amounts that the total antiperspirant metal ions (i.e., zirconium, aluminum and/or zinc) content of the formulation is between about 1.5 and 15 weight percent (depending on the type of formulation employed), calculated as the oxides of the metals.

For example, aqueous solutions of the complexes may be used in lotions, oil/water creams, and co-dispensing aerosols. The complexes of the present invention are not as a rule soluble in pure alcoholic solvent systems. However, the complexes may be considered for use in hydro-alcoholic mixed solvents, such as 75 percent ethanol and 25 percent water. In either the aqueous solutions or the hydro-alcoholic solvents, the complexes of the present invention should be present in the above antiperspirant forms in amounts such that the total content of antiperspirant metal ions in the formulation is on the order of about 5 to 15 weight percent (calculated as the oxides of the metals) or the formulation should contain 5 to 20 weight percent of the active ingredient (calculated on a solids basis).

The complexes of the present invention may also be used in the now popular powder-in-oil aerosol sprays. The powder-in-oil systems comprise the dispersion of a finely divided antiperspirant powder, such as the dried complexes of the present invention, in a non-solubilizing polar organic liquid such as an ester which serves as both a dispersion medium as well as an emollient. The organic liquid coats or wets the powder particles to render them heavier and more occlusive and/or substantive to the axillary region. This primary powder-in-oil suspension, known as the "concentrate", may also include a suspending or anti-compaction agent such as Cab-O-Sil or Bentone 34, to inhibit the dispersed phase from settling and compactng irreversibly. The so-called "extra-dry" formulations use less emollient and higher levels of dry powder, such as talc. Finally, after dynamic agitation the viscous concentrate is generally mixed with about 9 times its weight of a blend of standard propellants.

When used in the powder-in-oil aerosol sprays, the complexes of the present invention should be present in the finished formulation to the extent of about 1 to 6 weight percent, and preferably about 1.5 to 3 weight percent, total aluminum plus zirconium, calculated as the oxides. A typical powder-in-oil aerosol suspension would employ about 5 percent w/w of the active ingredient (dried complex) or about 2.5 percent total oxides.

Typical antiperspirant formulations employing the complexes of the present invention are exemplified in Table 1.

TABLE I

ANTIPERSPIRANT FORMULATIONS

| Ingredient | A*<br>Powder-in-oil aerosol | B*<br>Powder-in-oil extra-dry aerosol | C<br>Spray: (Manual-Pump) | D<br>Oil-in-water lotion | E<br>Oil-in-water cream |
|---|---|---|---|---|---|
| Active Ingredient (Antiperspirant) | | | | | |
| Complex of Example II | 3.5 | | | | |
| Complex of Example X | | | 10.0 | | |
| Complex of Example XIII | | 5.0 | | | |
| Complex of Example XIV | | | | 18.0 | 15.0 |
| Isopropyl Myristate | 6.0 | 3.0 | | | |
| Cab-O-Sil M-5[1] | 0.3 | 0.5 | | | |
| Perfume | 0.2 | | 0.5 | q.s. | q.s. |
| Propylene Glycol | | | 15.0 | | |
| Propellant 11 (trichlorofluoromethane) | 45.0 | 45.0 | | | |
| Propellant 12 (dichlorodifluoromethane | 45.0 | 45.0 | | | |
| Water | | | 19.5 | 66.0 | 56.0 |
| Alcohol SD-39C | | | 55.0 | | |
| Talc, U.S.P. | | 1.5 | | | |
| Arlacel 165[4] | | | | | 18.0 |
| Amerchol L-101[2] | | | | 5.0 | |
| Solulan 98[2] | | | | 2.0 | |
| Myrj 52[4] | | | | 4.0 | |
| Cetyle Alcohol | | | | 2.0 | |
| Glycerin | | | | 2.0 | 5.0 |
| Veegum HV[3] | | | | 1.0 | |
| Preservative | | | | q.s. | q.s. |
| Spermaceti | | | | | 5.0 |
| Titanium Dioxide | | | | | 1.0 |

[1]Cab-O-Sil M-5 - fumed amorphous silica of Cabot Corp.
[2]Amerchol L-101 and Solulan 98 - lanolin derivatives of Amerchol, Inc.
[3]Veegum HV - product of R. T. Vanderbilt & Co.
[4]Arlacel 165 and Myrj 52 - non-ionic emulsifiers of ICI America, Atlas Chem., Div.
*For "powder-in-oil" aerosols, active ingredient powders are ground before use in a micronizer to yield powders containing a particle size greater than 97% through a 325 mesh screen ($44\mu$).

In order to test the anitperspirant effectiveness of the complexes of the present invention, a powder-in-oil aerosol antiperspirant formulation of one of the complexes was prepared according to the following procedure:

A complex of ammonium zirconyl carbonate, zirconyl chloride and aluminum chlorhydroxide, prepared according to Example II above was spray dried to form a powder of the complex. A powder-in-oil aerosol containing 5 weight percent to this powder complex was then formulated by first preparing a concentrate consisting of 35 weight percent of the complex powder, 2 weight percent Cab-O-Sil M-5, 33 weight percent N-Butyl phthalate and 30 weight percent Freon 11. The aerosol can was filled using 28.7 grams of the concentrate and 81.3 grams of Freon 11 prior to crimping the valve on the container. 90 grams of Freon 12 was then pressure-filled into the can.

The above powder-in-oil aeorsol formulation was then tested by an independent testing laboratory against four other antiperspirant formulations. The five different formulations and the amounts of each used per application during the test are as follows:

Sample B — a 10 percent w/w refluxed aqueous solution of aluminum chlorhydrate (5/6 basic aluminum chloride). This solution was applied by swabbing in an amount of 0.5 ml per application.

Sample C — a 20 percent w/w alcoholic solution of basic aluminum bromide, as described in copending application Ser. No. 88,206 of Jones et al. for "Basic Aluminum Bromide Compositions". The sample was applied by a pump type sprayer as described in copending application Ser. No. 360,862 of Rubino et al. for "Method For Inhibiting Perspiration", and was applied in an amount of 6 squirts (0.6–1.0 grams) per application.

Sample D — an aqueous solution of a basic aluminum chloride-calcium complex, as described in my copending application Ser. No. 562,284, filed Mar. 26, 1975, entitled "Basic Calcium-Aluminum Compositions Useful As Antiperspirants". The solution was applied by swabbing in an amount of 0.5 ml per application.

Sample E. — the powder-in-aerosol formulation of a complex of the present invention, as described above. The formulation was applied as a two-second spray (3.0 grams) per application.

Sample F — an anhydrous antiperspirant stick formulation according to copending application Ser. No. 367,310 of Rubino et al. for "Anhydrous Antiperspirant Stick Compositions", and using Rehydrol as the active ingredient. This formulation was applied by rubbing the stick on the axilla so that an amount of approximately one gram was deposited per application.

The amounts for each application are believed to be roughly equivalent as to the amount of active ingredient applied. The test was run on fifteen male panelists from the Anderten/Hannover, Germany area. All panelists were required to abstain from use of all antiperspirants for two weeks prior to the test.

The study was carried out in five one-week test periods, with a two-week wash out period between each of the test weeks. Pre-treatment sweat measurements were made on Monday and Tuesday, and post-treatment measurements were made on Wednesday, Thursday and Friday of each test week. Only one axilla of each panelist was treated, and the other axilla was used as a control. Samples were assigned to panelists according to a cross-over pattern with each panelist being treated with a different sample in each of the five test weeks.

Sweating of the panelists was induced by having them sit in a room maintained at 100° F. at a relative humidity of about 35 percent. Sweat collections were made using weighed Webril pads.

Sample applications were made immediately following the control sweat collection on each Tuesday and one hour prior to the sweat collections on Wednesday and Thursday and immediately following sweat collections on Thursday of each test week. This provided evaluations one hour after each of the second and third applications and 22 hours after the fourth application.

A summary of the average percent sweat reduction for each sample, together with the 95 percent confidence limits, are set forth below.

| Sample | 1 Hour Combined Average | | 22 Hours After Application No. 4 | |
|---|---|---|---|---|
| B | 29.8 ± | 8.8% | 19.2 ± | 11.0% |
| C | 33.7 ± | 8.2% | 18.4 ± | 10.6% |
| D | 34.7 ± | 9.0% | 26.9 ± | 7.4% |
| E | 32.7 ± | 5.2% | 18.1 ± | 10.6% |
| F | 30.6 ± | 13.6% | 21.4 ± | 12.2% |

A demonstrated sweat inhibition of more than about 20 percent on a repeated application is regarded as substantially effective. As seen from the above Table, all samples had good activity one hour after application. The significant drop in sample activity after 22 hours may be explained by sample wash out (i.e. removal of axillary treatment by the flow of sweat in the area of the test site), since the panelists were athletic German men who generally had a rather strenuous work routine and were not controlled over the 22 hour period.

In any event, the formulation (Sample E) containing the complex of the present invention showed virtually equivalent antiperspirant activity to the other anitperspirant formulations tested, including the aluminum chlorhydrate sample, which is generally considered as the standard due to its long and widespread usage.

The present invention may be embodied in other specific forms without departing from the spirit or essential attributes thereof and, accordingly, reference should be made to the appended claims, rather than to the foregoing specification as indicating the scope of the invention.

I claim:

1. A stable, water soluble complex formed by reacting in aqueous medium components (a) and (b) as follows:
    a. a zirconyl carbonate selected from the group consisting of alkali metal zirconyl carbonate, ammonium zirconyl carbonate and mixtures thereof, and
    b. a water soluble, polyvalent metal salt of a strong acid, said polyvalent metal being selected from the group consisting of zirconium, aluminum, zinc, magnesium, calcium and mixtures thereof, whereby the zirconium in said zirconyl carbonate is converted to an acid, active antiperspirant species, said zirconyl carbonate being present in an amount of about 2 to 35 weight percent of the complex, the total zirconium in the complex comprising about 2 to 40 weight percent of the complex, and said polyvalent metal salt being present in an amount such that the complex will have a pH satisfactory for application to the human skin in an antiperspirant composition.

2. A complex according to claim 1 wherein said zirconyl carbonate comprises potassium zirconyl carbonate.

3. A complex according to claim 1 wherein said zirconyl carbonate comprises ammonium zirconyl carbonate.

4. A composition wherein the complex of claim 1 is dissolved in an aqueous medium such that the complex comprises about 5 to 20 weight percent (solids basis) of the solution and the solution has a pH of about 3 to 6.

5. A composition according to claim 1 wherein said zirconyl carbonate comprises sodium zirconyl carbonate.

6. A complex according to claim 1 wherein the anion of the polyvalent metal salt is selected from the group consisting of halide, sulfate, nitrate, sulfamate, phenolsulfonate, and mixtures thereof.

7. A complex according to claim 1 wherein said polyvalent metal salt comprises an aluminum compound selected from the group consisting of aluminum halide, basic aluminum halide and mixtures thereof.

8. A complex according to claim 1 wherein the only active antiperspirant metal in the complex is zirconium, and the total zirconium in the complex comprises about 8 to 30 weight percent of the complex.

9. A composition wherein the complex of claim 1 is in the form of a powder.

10. A powder-in-oil antiperspirant composition comprising an aerosol propellant, oil, and the complex according to claim 9, said complex being present in an amount of about 1 to 6 weight percent of the antiperspirant composition.

11. A complex according to claim 1 wherein said polyvalent metal salt comprises a zirconium compound selected from the group consisting of trioxodizirconium hydroxy salt and zirconium salts having the general empirical formula:

$$ZrO(OH)_{2-nz}B_z$$

wherein $z$ may vary from about 0.9 to 2 and need not be an integer, $n$ is the valence of B, $2-nz$ is greater than or equal to O, and B is selected from the group consisting of halide, nitrate, sulfamate, sulfate, and mixtures thereof.

12. A complex according to claim 1 which also includes an organic complexing agent selected from the group consisting of urea, an amino acid in which the number of amino groups is equal to the number of carboxyl groups in the molecule, an alkali metal salt of said amino acid, an alkaline earth metal salt of said amino acid, an ammonium salt of said amino acid, hydroxy aluminum salt of amino acid in which the number of amino groups is equal to the number of carboxyl groups, a hydroxy carboxylic acid having a hydroxyl group at least alpha to the carboxylic acid radical, a hydroxy carboxylic acid having a hydroxyl group at least beta to the carboxylic acid radical, aluminum chelate of hydroxy carboxylic acid having a hydroxyl group at least alpha to the carboxylic acid radical, aluminum chelate of hydroxy carboxylic acid having a hydroxyl group at least beta to the carboxylic acid radical, and mixtures thereof.

* * * * *